United States Patent [19]
Bergfeld et al.

[11] 4,210,602
[45] Jul. 1, 1980

[54] PROCESS FOR THE PREPARATION OF ASYMMETRICAL N-PHENYL-N'-SUBSTITUTED PARA-PHENYLENE DIAMINES

[75] Inventors: Manfred Bergfeld, Erlenbach; Hans G. Zengel, Kleinwallstadt, both of Fed. Rep. of Germany

[73] Assignee: Akzona Incorporated, Asheville, N.C.

[21] Appl. No.: 14,673

[22] Filed: Feb. 23, 1979

[30] Foreign Application Priority Data

Apr. 15, 1978 [DE] Fed. Rep. of Germany ....... 2816460

[51] Int. Cl.$^2$ ...................... C07C 85/08; C07C 85/11
[52] U.S. Cl. ..................................... 260/576; 252/439
[58] Field of Search ......................... 260/576; 252/439

[56] References Cited

FOREIGN PATENT DOCUMENTS

1295672  11/1972  United Kingdom ..................... 260/576

*Primary Examiner*—John Doll
*Attorney, Agent, or Firm*—Francis W. Young; Robert F. Green

[57] ABSTRACT

An improved process for the preparation of asymmetrical N-phenyl-N'-substituted para-phenylene diamines by the reductive alkylation of para-nitroso-diphenylhydroxylamine with an aldehyde or a ketone in the presence of hydrogen and a hydrogenation catalyst is disclosed. The improvement comprises utilizing as the hydrogenation catalyst (1) one member selected the group consisting of palladium and platinum sulfide, in an amount less than 1%, by weight, based on the weight of para-nitroso-diphenylhydroxylamine, and (2) activated carbon with a specific surface area of at least 700 square meters per gram and an ash content of less than 7.5%, by weight.

11 Claims, No Drawings

“4,210,602”

PROCESS FOR THE PREPARATION OF ASYMMETRICAL N-PHENYL-N'-SUBSTITUTED PARA-PHENYLENE DIAMINES

BACKGROUND OF THE INVENTION

This invention relates to a process for the preparation of asymmetrical N-phenyl-N'-substituted para-phenylene diamines by the reductive alkylation of para-nitroso-diphenylhydroxylamines with an aldehyde or a ketone in the presence of hydrogen and a hydrogenation catalyst.

The reductive alkylation of nitroso compounds by reaction with an aldehyde or a ketone in the presence of hydrogen and an hydrogenation catalyst is known in the art. Thus, use of certain metal compounds as hydrogenation catalysts, such as copper chromite (British Patent No. 804,113 and Russian Patent No. 230,828), nickel sulfide (East German Published Patent Appleiation No. 1,542,171), a selenide, a telluride, or a nickel chromium catalyst (Czecholslovakian Patent No. 119,336), or mixtures of two or more heavy metals, iron, manganese, copper, chromium, nickel, silver, cerium or lead, in the form of their oxides, hydroxides, or carbonates (East German Patent Disclosure No. 1,941,009) is known. However, all of the catalysts used in accordance with the foregoing prior art procedures produce side reactions, in particular, reduction of the aldehyde or ketone to the corresponding alcohol.

According to the process for the preparation of N-phenyl-N'-alkyl-para-phenylene diamines disclosed in British Patent No. 1,295,672, para-nitroso-diphenylhydroxylamine is reacted with hydrogen and an aldehyde or a ketone in the presence of a hydrogenation catalyst at temperatures in the range from room temperature to 200° C. The hydrogenation catalyst utilized is made of a metal from Group VIII of the periodic system, such as nickel, cobalt, ruthenium, palladium, or platinum, which, if desired, may have been deposited on an inert carrier material, such as carbon, aluminum oxide, or silica gel. Yields of N-phenyl-N'-alkyl- and N-phenyl-N'-cycloalkyl-para-phenylene diamines of about 95% of theoretical are indeed obtained by the foregoing process, but for an industrial scale preparation of such products, the yield and selectivity achieved thus far are inadequate. Furthermore, the required catalyst quantities are too large and the losses of catalyst are thus considerable.

Therefore, an object of the present invention is to provide a process for the preparation of asymmetrical N-phenyl-N'-substituted para-phenylene diamines by reductive alkylation of para- nitroso-diphenylhydroxylamines with an aldehyde or a ketone in the presence of a hydrogenation catalyst, which process does not suffer from the foregoing drawbacks and results in the production of the desired compounds in high yields.

SUMMARY OF THE INVENTION

An improved process for the preparation of asymmetrical N-phenyl-N'-substituted para-phenylene diamines by the reductive alkylation of para-nitroso-diphenylhydroxylamine with an aldehyde or a ketone in the presence of hydrogen and a hydrogenation catalyst is thus provided. The improvement comprises utilizing as the hydrogenation catalyst (1) one member selected from the group consisting of palladium and platinum sulfide, in an amount less than 1%, based on the weight of para-nitroso-diphenylhydroxylamine, and (2) an activated carbon with a specific surface area of at least 700 square meters per gram and an ash content of less than 7.5%, by weight. Optionally, the process may be preformed in the presence of an inert solvent.

DESCRIPTION OF THE PREFERRED EMBODIMENTS

Para-nitroso-diphenylhydroxylamine is a compound which may be readily obtained by means of the catalytic dimerization of nitrosobenzene. According to a recent, especially advantageous process, the foregoing compound may be obtained with practically quantitative yield, if a sulfonic acid with a $pK_a \leq 1$, for example methane-, ethane-, or trifluoromethanesulfonic acid, or perchloric or trifluoroacetic acid is used as a catalyst (German Patent Application No. P 27 03 919). The nitrosobenzene required for the preparation of para-nitroso-diphenylhydroxylamine is likewise easily accessible and may be obtained by the catalytic reduction of nitrobenzene. The reduction will proceed with a high conversion rate and high selectivity if, pursuant to another recent process, an aliphatic, cycloaliphatic, olefinic, or aromatic hydrocarbon is used as the reducing agent (German Patent Application No. P 27 13 602).

In each instance, the compounds obtainable pursuant to the present invention have a phenyl radical as a substituent on the N atom, whereas the N' atom carries one or two aliphatic, cycloaliphatic, or aromatic substituents. In the latter instance, the substituents may be the same or different. Selection of the aldehyde or ketone to be utilized depends, of course, upon the desired para-phenylene diamine derivative. For the preparation of N-phenyl-N'-monosubstituted para-phenylene diamines, one may utilize an aldehyde in the reaction and for the preparation of N-phenyl-N'-disubstituted para-phenylene diamines one may utilize a ketone. Examples of suitable carbonyl compounds are: aliphatic aldehydes, such as formaldehyde; alkyl-alkyl ketones, such as acetone; cyclic ketones, such as cyclobutanone; aryl-aryl ketones, such as benzophenone; alkyl-aryl ketones, such as acetophenone and methylbenzyl ketone; alkyl-cycloalkyl ketones, such as methylcyclohexyl ketone; aryl-cycloalkyl ketones, such as phenylcyclohexyl ketone; aromatic aldehydes, such as benzaldehyde; cyclic aldehydes, such as cyclohexyl aldehyde; and diketones, such as 2,4-pentanedione.

The process pursuant to the present invention is preferably utilized for the preparation of N-phenyl-N'-monoalkyl-para-phenylene diamines, N-phenyl-N'-dialkyl-para-phenylene diamines and N-phenyl-N'-cycloalkyl-para-phenylene diamines. In such instances, aldehydes, alkyl-alkyl ketones, and cyclic ketones are utilized.

Examples of suitable aldehydes are: formaldehyde, acetaldehyde, propionaldehyde, butyraldehyde, and valeraldehyde. Examples of suitable alkyl-alkyl ketones are: acetone, methylethyl ketone, methyl-propyl ketone, methyl-butyl ketone, methylisobutyl ketone, methyl-amyl ketone, methyl-isoamyl ketone, methyl-hexyl ketone, methyl-heptyl ketone, methyl-octyl ketone, diethyl ketone, ethyl-propyl ketone, ethyl-butyl ketone, ethylamyl ketone, ethyl-hexyl ketone, ethyl-heptyl ketone, 5-methylheptanone-(3), dipropyl ketone, dibutyl ketone, diisobutyl ketone, diamyl ketone, dihexyl ketone, diheptyl ketone, and diisodecyl ketone. Examples of suitable cyclic ketones are: cyclobutanone, cyclopentanone, cyclohexanone, and cyclooctanone.

In the process of the present invention it is not absolutely necessary to use pure hydrogen. Thus, one may use carrier gases, such as nitrogen, and gas mixtures, which, in addition to hydrogen, also contain carbon monoxide, such as water gas and generator gas. In such instances, the carbon monoxide also participates in the reaction, however, enough hydrogen should be present, so that a complete reduction is guaranteed.

The customary palladium or platinum sulfide catalyst is used as the hydrogenation catalyst, such as catalysts with the usual types of carbon as carrier, such as coal, lamp black, and activated carbon. The term "platinum sulfide" is utilized herein to mean commercially available "sulfidized platinum", obtained by sulfidizing platinum. Although a specific platinum sulfide is not involved here, such catalysts are, for the sake of simplicity, referred to as platinum sulfide in the industry (cf. Robert I. Peterson, Hydrogenation Catalysts, Noyes Data Corporation, Parkridge, N.J., USA, 1977, pp. 256–261). In contrast to the kind of activated carbon to be additionally used as catalyst, the kind of carrier material is of only nominal importance. Preferably, however, an activated carbon with a specific surface area of at least 700 $m^2/g$ and an ash content of less than 7.5%, by weight, is likewise utilized as the carrier material.

Reductive alkylation of the para-nitroso-diphenylhydroxylamine will largely proceed without problems if, as in the customary processes, catalyst quantities of more than one percent, by weight, of palladium sulfide or platinum sulfide, based on the initial material, are utilized. However, such large catalyst quantities substantially increase the cost of synthesis, especially since the losses of catalyst are also considerable. Furthermore, excessive hydrogenation will result in the formation of products which are hydrogenated in the nucleus, the separation of which, from the desired N-phenyl-N'-substituted para-phenylene diamines, is difficult. In addition, there is the possibility of hydrogenation of the excess carbonyl compound which may be present as solvent, to an undesirable alcohol (cf. comparative example).

In the process pursuant to the present invention, the hydrogenation catalyst is used in a quantity corresponding to less than 1%, by weight, of palladium, or platinum sulfide, based on the para-nitroso-diphenylhydroxylamine, preferably in quantities of from about 0.05 to about 0.2%, by weight, of palladium or platinum sulfide. The formation of alcohol by hydrogenation of excess carbonyl compound, if any, is thus almost completely eliminated. Under such conditions, there is likewise no hydrogenation of the nucleus of the desired N-phenyl-N'-substituted para-phenylene diamines.

The hydrogenation catalyst consisting of palladium or platinum sulfide typically on a carbon carrier material may contain from about 0.05 to about 10%, by weight, of palladium or platinum sulfide. Preferably, the catalyst is endowed with from about 0.5 to about 5%, by weight, of palladium or platinum sulfide. In particular, use may be made of the commercially available precious metal/carbon catalysts, which contain from about 1 to about 5%, by weight, of palladium or platinum sulfide. Consequently, depending upon the endowment with precious metal, the quantity of hydrogenation catalyst based on para-nitroso-diphenylhydroxylamine at most amounts to from about 0.1%, by weight (with 10% precious metal endowment), to about 20%, by weight (with 0.05% precious metal endowment).

Surprisingly, it has been found that, pursuant to the present invention, the concomitant use of activated carbon as catalyst in conjunction with the palladium or platinum sulfide catalyst, considerably increases the selectivity, as well as the yield of the reductive alkylation and, in a continuous operation, results in considerable lengthening of the life of the catalyst system. It is peculiar, that this effect is pronounced only with palladium and platinum sulfide catalysts, whereas it is barely noticeable with other catalyst metals.

The nature of the activated carbon to be used as the additional catalyst is essential to the invention. It has thus been found that the catalytic effectiveness occurs only with highly active types of activated carbon. The specific surface area of the activated carbon has to be at least about 700 $m^2/g$. The ash content, which as to be less than about 7.5%, by weight, is also decisive for the catalytic effectiveness of the activated carbon. The term "ash content" as used herein means the insoluble, as well as the soluble, ash constituents. As a rule, activated carbon types obtained from natural initial materials, such as lignite, peat, wood, bones, and the like, contain substantially greater quantities of ash and are therefore not suitable without further processing for use in the process pursuant to the present invention. However, if the ash content is reduced to less than 7.5%, by weight, by careful washing with acids, and if the required large specific surface area is present, such activated carbon types may be utilized.

Trace elements evidently have no, or perhaps only a subordinate, influence on the effectiveness of the carbon catalyst. The selection of suitable carbon types is therefore governed by the two above-mentioned criteria. Although all activated carbons with a specific surface area of more than about 700 $m^2g$ and an ash content of less than about 7.5%, display catalytic activity in the process pursuant to the present invention, activated carbons prepared from petroleum, natural gas, anthracite, or cellulose are preferred because of their purity.

The quantity of activated carbon catalyst to be used is from about 10 to about 200%, by weight, based on the weight of para-nitroso-diphenylhydroxylamine. The exact quantity depends upon the quantity of precious metal based upon the para-nitroso-diphenylhydroxylamine and upon the endowment with precious metal in the hydrogenation catalyst, that is upon the quantity ratio of precious metal:carrier carbon. In order to obtain the same yield level, a reduction in precious metal quantity requires an increase in activated carbon catalyst quantity. The following correlation exists between the endowment of the hydrogenation catalyst with precious metal and the required quantity of activated carbon catalyst: In the range of a precious metal endowment of the hydrogenation catalyst of about 1 to about 10%, by weight, the quantity of activated carbon catalyst required for the same level of conversion declines with declining endowment of precious metal. In the range of endowment with precious metal of about 0.05 to about 1%, by weight, a declining endowment with precious metal requires increasing quantities of activated carbon catalyst, in order to obtain the same level of conversion.

In the preferred version of the process pursuant to the present invention use is made of from about 0.01 to about 20%, by weight, of the palladium, or platinum sulfide catalyst, on a carbon carrier (with from about 0.05 to about 0.2%, by weight, of the metal) and from about 10 to about 200%, by weight, of activated carbon as additional catalyst, all based on the weight of para-nitroso-diphenylhydroxylamine.

The quantity of aldehyde or ketone typically amounts to from about 1 to about 10 equivalents, per equivalent of para-nitroso-diphenylhydroxylamine, preferably to from about 2 to about 10 equivalents. It is also possible to use greater quantities of aldehyde or ketone, in which instance the excess serves as solvent.

If desired, other inert solvents (co-solvents) may also be used, for example, aliphatic or aromatic hydrocarbons, their halogen derivatives or ethers, such as toluene, monochlorobenzene, dichlorobenzene, 1,2,4-trichlorobenzene, or 1,1,2-trifluoro-1,1,2-trichloroethane. Especially suitable inert solvents are the lower alcohols, such as methanol, ethanol, isopropanol, propanol, butanol, pentanols, isopentanols, and 4-methylpentanol-2. The use of inert solvents is particularly advantageous when the water of reaction formed in the course of the reaction is not, or is only slightly, soluble in the ketone or aldehyde utilized, so that an aqueous phase is formed in addition to the organic one. In cases in which the aldehyde or ketone is miscible with water to such an extent that a second phase will not form, it is preferable not to use an additional solvent.

In the process pursuant to the present invention one may also use para-nitroso-diphenylhydroxylamine wetted with water, which contains up to 100%, by weight, of water. Here, the water is also a co-solvent. It is also not necessary that the para-nitroso-diphenylhydroxylamine be present in dissolved form, so that the reaction takes place in a homogeneous phase. Preferably, the conversion is carried out in a heterogeneous phase. This is advantageous in that the reaction volume is relatively small and the processing of the reaction mixture is expedited.

The process pursuant to the present invention can be carried out batchwise, as well as continuously. The reaction temperature and the reaction pressure are not critical. The process pursuant to the present invention may be performed at normal pressure and room temperature, but, because of the influence of pressure and temperature on the reaction rate, it is expedient to perform the reaction at elevated temperatures and elevated pressures. Generally, it is advisable to work within a temperature range from about 20° to about 150° C. The preferred reaction temperature is from about 25° to about 125° C., most preferably from about 40° to about 100° C. The hydrogen pressure may be anywhere within a wide range, as from about 1 to about 150 bar. Preferably the hydrogen pressure is from about 5 to about 15 bar, most preferably from about 7 to about 12 bar. As a general rule, the reaction time is typically from about 15 minutes to about 5 hours, preferably from about 0.05 to about 3 hours.

The reaction mixture may be processed in a typical manner. First, the catalyst may be filtered off, then the solvent siphoned off, if necessary, and subsequently the amine may either be distilled or crystallized. The method suitable in the particular case depends upon the physical characteristics of the amine and the solvent utilized. The solvent may be circulated, if desired. In a classical prior art process, the catalyst is partially contaminated after the reductive alkylation has been carried out and when re-used, the catalyst displays a reduced activity, so that in practice it must be supplemented by a certain quantity of fresh catalyst. In contrast thereto it has been found from the process pursuant to the present invention that, due to the addition of the activated carbon catalyst, the used hydrogenation catalyst retains its activity for a lengthy period of time so that when it is re-used, none, or comparatively small quantity of fresh hydrogenation catalyst must be added in order to reach the original activity. For example, if a catalyst with 0.2%, by weight, of palladium, based on the para-nitroso-diphenylhydroxylamine, is used in a reductive alkylation process pursuant to the present invention, only an additional 0.01%, by weight, of palladium, is required in the second reaction cycle. After a few additional reaction cycles, the quantity of supplementary, fresh catalyst required for some of the catalyst activity declines to only 0.005%, by weight. Finally, several additional reaction cycles can even be carried out without any further fresh hydrogenation catalyst.

It is not necessary to supply fresh activated carbon catalyst in every new reaction cycle. On the average, the consumption of hydrogenation catalyst per reaction cycle is thus less than 0.01%, by weight, of palladium, based on the charged para-nitroso-diphenylhydroxylamine. If, for example, in the case of methylisobutyl ketone, a catalyst with 0.2%, by weight, of platinum sulfide and 100%, by weight, of activated carbon within the scope of the present invention, based on the para-nitroso-diphenylhydroxylamine are utilized, 15 additional reaction cycles can be carried out without any loss in activity of the catalyst system. When the same series is performed without activated carbon, the yield of N-(1,3-dimethylbutyl)-N'-phenyl-para-phenylene diamine (DBPPD) is only 60% of theoretical in the first cycle (vs. 95% of theoretical with activated carbon present), while in the second cycle it immediately drops to 38% of theoretical (vs. an unchanged yield of 95% of theoretical in the presence of activated carbon).

Compared with the prior art process of British Patent No. 1,295,672, the process pursuant to the present invention is substantially more advantageous. For example, according to Example 1 of the British patent, N-isopropyl-N'-phenyl-para-phenylene diamine (IPPD) is allegedly obtainable with a 93% yield. However, a true yield of a desired substituted para-phenylene diamine apparently in reality, was not achieved, as the amount of reaction product remaining after distillation of the solvent was improperly assumed to consist entirely of the desired substance. As is discovered when the example is reproduced, the initial material is indeed converted quantitatively, but the reaction product is a mixture of substances with a share of only about 78% of N-isopropyl-N'-phenyl-para-phenylene diamine (IPPD). In addition, the large quantity of 0.3%, by weight, of palladium, based on the para-nitroso-diphenylhydroxylamine, as well as the long reaction time, are required and the reaction is performed under a pressure of 50 bar. As a result, one gets not only higher losses of N-isopropyl-N'-phenyl-para-phenylene diamine (IPPD), but the excess ketone is also substantially reduced to an undesirable alcohol.

The process pursuant to the present invention, on the other hand, requires lower pressures and temperatures, smaller quantities of precious metal catalysts, and substantially shorter reaction times. Furthermore, the selectivity, with respect to the formation of the desired substituted para-phenylene diamine, is substantially higher and the formation of alcohol by reduction of the carbonyl compound does not occur. When the process of the British patent is carried out at lower temperatures, for example, at less than 150° C., and with lower pressures, for example below 50 bar, the reaction proceeds much less selectively than under the more drastic conditions. The reason is that one obtains about 25 to about 50% of the non-alkylated reaction product and about 2.5 to about 10% of the ketimine, as by-products. The yield of the desired substituted para-phenylene diamine is only from about 12 to about 70%, the remainder consisting of unreacted initial compound and the aforementioned by-products. The process pursuant to the present invention is thus distinguished by the fact that it is performed at a comparatively low pressure and temperature with low consumption of precious metal, leading to the formation of the desired product within short reaction times and producing a high conversion rate with associated high selectivity.

Large quantities of compounds obtainable by the process pursuant to the present invention are useful industrially for the antioxidation and ozonation of rubber.

COMPARATIVE EXAMPLES NOS. 1 to 9

The reactions are carried out in a 1 liter glass autoclave equipped with a bottom drain valve, a gas supply tube, a flow breaker, and a vaned stirrer (magnetic stirring). 20 g (93.2 mmol) of para-nitroso-diphenylhydroxylamine (NDHA) and 200 ml of acetone are charged and the reaction is carried out between 30° and 75° C., with hydrogen pressure between 9 and 10 bar. The reaction lasts for approximately one hour and the stirring velocity is 1,500 rpm. The autoclave is first evacuated, then vented with hydrogen. Subsequently, the autoclave is charged with half of the reaction medium, and finally the para-nitroso-diphenylhydroxylamine (NDHA), together with the palladium/carbon catalyst (E10R of the firm Degussa), is suspended in the remainder of the reaction medium and fed in via the inlet valve. Subsequently, the autoclave is placed under a pressure of 9 to 10 bar of hydrogen, and heated carefully. Depending upon the quantity of palladium, the reaction commences between 20° and 70° C. After the heat of reaction declines, heating to 75° C. is continued, so that the total reaction time amounts to approximately 1 hour.

Table I shows the influence of the quantity of precious metal on the yield of N-isopropyl-N'-phenyl-para-phenylene diamine (IPPD). The composition of the palladium/carbon catalyst, the quantity of metal based on the charged para-nitroso-diphenylhydroxylamine, as well as the yields of asymmetrical N-phenyl-N'-substituted-para-phenylene diamine and the quantity of ketimines formed as by-product and non-alkylated paraphenylene diamine derivatives are compiled in Table I.

The following abbreviations are used in the Table:
NDHA = para-nitroso-diphenylhydroxylamine
ADA = 4-amino-diphenylamine
IPPD = N-isopropyl-N'-phenyl-para-phenylene diamine
ketimine = N-isopropylidene-N'-phenyl-para-phenylene diamine.

The results contained in Table I show, in an impressive manner, that with the use of a catalyst quantity corresponding to 1%, by weight, based on the para-nitroso-diphenylhydroxylamine, the reductive alkylation to the desired N-isopropyl-N'-phenyl-para-phenylene diamine still proceeds with relatively high selectivity. However, when smaller catalyst quantities are utilized, the selectivity, with respect to the formation of N-isopropyl-N'-phenyl-para-phenylene diamine declines rapidly. With catalyst quantities of 0.20%, by weight, of palladium, the selectivity is already considerably below 10%.

Table I

| | | | | | Hydrogenation Catalyst E10R | | | | | |
| --- | --- | --- | --- | --- | --- | --- | --- | --- | --- | --- |
| Example No. | NDHA | | Solvent Acetone | | Endowment % by Wt. of Pd | % by Wt. Pd. Ref. to NDHA | Reaction Products in % by Weight | | | |
| | g | m.mol | ml | g | | | IPPD | ADA | Ketimine | NDHA |
| 1 | 20.0 | 93.2 | 200 | 4.0 | 5 | 1.0 | 94.3 | <0.1 | <0.2 | <0.1 |
| 2 | 20.0 | 93.2 | 200 | 3.0 | 5 | 0.75 | 92.6 | 1.1 | 0.65 | <0.1 |
| 3 | 20.0 | 93.2 | 200 | 2.0 | 5 | 0.50 | 86.3 | 2.2 | 3.6 | <0.1 |
| 4 | 20.0 | 93.2 | 200 | 1.0 | 5 | 0.25 | 68.2 | 26.7 | 2.4 | 1–2 |
| 5 | 20.0 | 93.2 | 200 | 0.80 | 5 | 0.20 | 58.1 | 48.4 | 3.2 | ~5 |
| 6 | 20.0 | 93.2 | 200 | 0.50 | 5 | 0.125 | 40.2 | 50.2 | 3.5 | ~7 |
| 7 | 20.0 | 93.2 | 200 | 0.40 | 5 | 0.10 | 12.7 | 76.8 | 7.6 | ~10 |
| 8 | 20.0 | 93.2 | 200 | 0.20 | 5 | 0.05 | 7.1 | 48.3 | 28.7 | ~15 |
| 9 | 20.0 | 93.2 | 200 | 0.040 | 5 | 0.01 | 2.8 | 28.9 | 49.8 | ~20 |

EXAMPLES 10 through 21

The conversion rate, as well as the selectivity, obtained pursuant to the process of the present invention, by the addition of of activated carbon with a surface area of at least 700 m$^2$/g and an ash content less than 7.5%, by weight, is easily recognizable from these examples, and the comparative examples contained in Table II. For this purpose, Example 7 of Table I was repeated once with, and once without, the addition of activated carbon, and the conversion rate, as well as the yield were determined quantitatively after different reaction times.

In each case, 60 g (280 mmol) of para-nitroso-diphenylhydroxylamine and 600 ml of acetone are reacted in the manner described for Examples 1 through 9 in the presence of 6.0 g of a palladium/carbon catalyst (E10R of the firm Degussa) with a palladium endowment of 1.01%, by weight, a specific surface area of 1100 m$^2$/g and an ash content of ≦0.5%, by weight. In the cases of Examples 17, 19, and 21, the yield of N-isopropyl-N'-phenylpara-phenylene diamine is lower than, for example, in the case of Example 15, since, because of the long reaction times, reduction of part of the desired product has to be continued to form N-isopropyl-N'-cyclohexyl-para-phenylene diamine.

Table II

| Example No. | NDHA g | NDHA mmol | Solvent Acetone ml | Hydrogenation Catalyst % by Wt. | Hydrogenation Catalyst Pd Ref. to NDHA | React. Time Min. | A. Carbon % by Wt. Ref. to NDHA | Reaction Products in % by Wt. IPPD | ADA | Ketimine | NDHA |
|---|---|---|---|---|---|---|---|---|---|---|---|
| 10* | 60 | 280 | 600 | 6.0 | 0.1 | 15 | — | 2.2 | 43.5 | 23.2 | 25 |
| 11 | 60 | 280 | 600 | 6.0 | 0.1 | 15 | 100 | 90.0 | 6.4 | 1.8 | <1 |
| 12* | 60 | 280 | 600 | 6.0 | 0.1 | 30 | — | 7.8 | 50.2 | 15.2 | 18 |
| 13 | 60 | 280 | 600 | 6.0 | 0.1 | 30 | 100 | 95.0 | 0.95 | 0.5 | <0.1 |
| 14* | 60 | 280 | 600 | 6.0 | 0.1 | 60 | — | 12.7 | 76.0 | 7.6 | 10 |
| 15 | 60 | 280 | 600 | 6.0 | 0.1 | 60 | 100 | 96.5 | 0.1 | 0.2 | <0.1 |
| 16* | 60 | 280 | 600 | 6.0 | 0.1 | 120 | — | 17.7 | 58.0 | 18.5 | 5 |
| 17 | 60 | 280 | 600 | 6.0 | 0.1 | 120 | 100 | 95.5 | 0.1 | 0.1 | <0.1 |
| 18* | 60 | 280 | 600 | 6.0 | 0.1 | 180 | — | 24.2 | 50.5 | 12.8 | ~ |
| 19 | 60 | 280 | 600 | 6.0 | 0.1 | 180 | 100 | 91.5 | 0.1 | 0.1 | <0.1 |
| 20* | 60 | 280 | 600 | 6.0 | 0.1 | 300 | — | 22.5 | 68.5 | 5.5 | <1 |
| 21 | 60 | 280 | 600 | 6.0 | 0.1 | 300 | 100 | 89.5 | 0.1 | 0.1 | <0.1 |

*Comparative Example

EXAMPLES 22 THROUGH 32

To a 1.5 liter glass autoclave, equipped with vaned stirrer, thermometer, gas supply tube, manometer, flow breaker, gas outlet valve, bottom discharge valve, and filter candle, there is charged a suspension of 20 g of para-nitroso-diphenylhydroxylamine and 0.8 g of palladium/carbon catalyst (E10R of the firm Degussa) with an endowment of 5% of palladium (0.20%, palladium, based on the para-nitroso-diphenylhydroxylamine), as well as 25 g of activated carbon (Merck, in powder form, dried, with a specific surface area of 1050 m²/g, ash content less than 5%, by weight) and 200 ml of methylisobutyl ketone. After repeated evacuation and venting with hydrogen, the reaction was started under a hydrogen pressure of 9 to 10 bar. The reductive alkylation is started at about 40° C. and, after cooling of the exothermic reaction, heating to 75° C. is continued for a total of 1 hour, with a stirring velocity of 1500 rpm. After termination of the reaction, the substrate is separated from the hydrogenation catalyst and the activated carbon catalyst, which afterwards are flushed back into the autoclave with methylisobutyl ketone, via the filter candle under hydrogen pressure. Subsequently, the following batch, consisting of 20 g of para-nitroso-diphenylhydroxylamine and a total of 200 g of methylisobutyl ketone are mixed with activated carbon catalyst and, if necessary, fresh hydrogenation catalyst, and again reacted for 1 hour at 75° to 80° C. and a hydrogen pressure of 9 to 10 bar. These experiments were carried out for a total of 10 cycles, so that at the end of the conversion a total of 220 g of para-nitroso-diphenylhydroxylamine are subjected to reductive alkylation.

The quantities of hydrogenation catalyst, as well as the quantity of activated carbon catalyst, indicated in %, by weight, of palladium, based on the total par-nitroso-diphenylhydroxylamine charged, as well as the resulting yield of N-(1,3-dimethylbutyl)-N'-phenyl-para-phenylene diamine (DBPPD), para-amino-diphenylamine (ADA), and ketimine are lised in Table III. The results clearly show that after a few reaction cycles, the quantity of fresh hydrogenation catalyst to be added declines considerably.

Table III

| Example No. | NDHA g | NDHA mmol | Solvent MIBK ml | Hydrogenation Catalyst g | Hydrogenation Catalyst % by Wt. Pd Ref. to NDHA | Act. Carbon g | Act. Carbon % by Wt. | Reaction Products in % by Wt. DBPPD | ADA | Ketimine | NDHA |
|---|---|---|---|---|---|---|---|---|---|---|---|
| 22 | 20 | 93.2 | 200 | 0.8 | 0.20 | 25 | 120 | 95 | 0.1 | 0.5 | <0.1 |
| 23 | 40 | 186.4 | 400 | 1.2 | 0.15 | 25 | 62.5 | 93 | 0.5 | 1.0 | ~0.5 |
| 24 | 60 | 279.6 | 600 | 1.2 | 0.10 | 30 | 50 | 95 | 0.1 | 0.5 | <0.1 |
| 25 | 80 | 372.8 | 800 | 1.2 | 0.075 | 30 | 37.5 | 86 | 1.7 | 2.8 | ~1 |
| 26 | 100 | 466 | 1000 | 1.5 | 0.075 | 40 | 40 | 95 | 0.3 | 0.5 | <0.1 |
| 27 | 120 | 599.2 | 1200 | 1.5 | 0.0625 | 40 | 33.3 | 88 | 2.8 | 4.5 | <1 |
| 28 | 140 | 652.4 | 1400 | 1.5 | 0.0536 | 50 | 35.7 | 92.5 | 0.6 | 1.2 | <0.1 |
| 29 | 160 | 745.6 | 1600 | 1.5 | 0.047 | 50 | 31.25 | 83 | 3.6 | 5.9 | ~2 |
| 30 | 180 | 838.8 | 1800 | 1.5 | 0.0416 | 65 | 36 | 91 | 1.0 | 1.3 | ~0.5 |
| 31 | 200 | 932.0 | 2000 | 1.5 | 0.0375 | 65 | 32.5 | 44 | 18.0 | 33.0 | ~5 |
| 32 | 220 | 1025.2 | 2200 | 1.5 | 0.034 | 85 | 38.6 | 78.5 | 3.5 | 2.5 | ~1 |

EXAMPLES 33 THROUGH 45

In these examples, and comparative examples, the influence of the quantity of added activated carbon (Examples 33 to 36), as well as the influence of the type of activated carbon (Examples 37 to 45) on the progress of reductive alkylation is demonstrated.

The reactions are carried out in the manner described for Examples 1 through 9 and in each case, 20 g of para-nitrosodiphenylhydroxylamine (NDHA) and 150 ml methylisobutyl ketone (MIBK) are charged. The hydrogenation catalyst is a palladium/carbon catalyst (E106R of the firm Degussa) with 1.02%, by weight, of palladium endowment. The types of activated carbon are synthetic carbons of the firms Degussa and Merck, with different specific surfaces and ash contents, as well as various activated carbons from natural raw materials.

Comparative examples 42 through 45 clearly show that in the case of too small of a specific surface area, as well as in the case of too high of an ash content of the activated carbons, the yields of N-(1,3-dimethylbutyl)-N'-phenyl-para-phenylene diamine (DBPPD) are low.

Table IV

| Example No. | NDHA g | MIBK ml | Hydrog. Catal. g | % by Wt. Pd Ref. to NDHA | % by Wt. Ref. To NDHA | Type | Spec. Surface m²/g | Ash, % | DBPPD | ADA | Ketimine | NDHA |
|---|---|---|---|---|---|---|---|---|---|---|---|---|
| 33* | 20 | 150 | 2.0 | 0.1 | — | — | — | — | 63.0 | 15.5 | 16.0 | ~2 |
| 34 | 20 | 150 | 2.0 | 0.1 | 50 | R10 | 900–950 | 0.7–0.75 | 86.5 | 4.65 | 4.5 | <0.1 |
| 35 | 20 | 150 | 2.0 | 0.1 | 100 | R10 | 900–950 | 0.7–0.75 | 94.0 | 1.29 | 1.1 | <0.1 |
| 36 | 20 | 150 | 2.0 | 0.1 | 150 | R10 | 900–950 | 0.7–0.75 | 95.5 | 1.12 | 0.9 | <0.1 |
| 37 | 20 | 150 | 2.0 | 0.1 | 50 | R101 | 1100 | 1.0 | 92.5 | 2.4 | 2.7 | <0.1 |
| 38 | 20 | 150 | 2.0 | 0.1 | 50 | R102 | 900 | 4.7 | 73.2 | 14.2 | 9.9 | <0.1 |
| 39 | 20 | 150 | 2.0 | 0.1 | 50 | R103 | 1000 | 0.72 | 89.5 | 4.5 | 3.28 | <0.1 |
| 40 | 20 | 150 | 2.0 | 0.1 | 50 | R106 | 950 | 0.53 | 86.5 | 5.6 | 5.4 | <0.1 |
| 41 | 20 | 150 | 2.0 | 0.1 | 50 | R106 | 1000 | 0.44 | 85.5 | 6.65 | 4.8 | <0.1 |
| 42* | 20 | 150 | 2.0 | 0.1 | 50 | Merck Purest | 1000–1050 | 0.63 | 88.5 | 4.5 | 4.0 | <0.1 |
| 43* | 20 | 150 | 2.0 | 0.1 | 50 | Animal Carbon | 150 | 78.5 | 57.0 | 22.7 | 17.5 | ~5 |
| 44* | 20 | 150 | 2.0 | 0.1 | 50 | Linden Wood Carbon | 300 | 3.65 | 29.5 | 26.9 | 40.0 | ~2 |
| 45* | 20 | 150 | 2.0 | 0.1 | 50 | Beech Wood Carbon | 450 | 4.78 | 51.5 | 19.9 | 25.5 | ~5 |

*Comparative Example

EXAMPLES 46 THROUGH 55

In these examples, the results of which are compiled in Table V, it is demonstrated that in the process pursuant to the present invention the used hydrogenation catalyst retains its activity for an extended period of time when activated carbon catalyst is added, even in the presence of larger quantities of N-phenyl-N'-substituted para-phenylene diamines (end product) so that when it is used again, no, or comparatively small quantities of fresh hydrogenation catalyst must be added, to reach the original activity again. Furthermore, the favorable influence is shown which an additional inert solvent (cosolvent) exerts in those instances where the formed water of reaction is not, or is only slightly soluble, in the ketone used for the reductive alkylation, and a second, aqueous phase would be formed without addition of the cosolvent.

The reactions are carried out in a 1.5 liter apparatus already described in conjunction with Examples 22 through 32. The reaction temperatures are from 75° to 100° C., the hydrogen pressure is from 9 to 10 bar, the duration of the reaction is 1.5 hours, and the stirring velocity is 1000 to 1500 rpm. After each cycle, a small sample is taken for an analytical determination of the reaction mixture, whereupon in each instance the following batch consisting of 10 g of para-nitroso-diphenylhydroxylamine (NDHA), 50 ml each of cyclohexanone, and cosolvent, and, depending upon the experiment, an additional quantity of activated carbon catalyst, or fresh palladium/carbon catalyst, is added through the inlet valve to the already complete reaction mixture under hydrogen pressure. The experiments are continued through a total of 10 cycles, so that at the end of the reactions, a total of 100 g of para-nitroso-diphenylhydroxylamine (NDHA) with cyclohexanone have been subjected to reductive alkylation.

Table V

| Example No. | NDHA g | Cyclo-hexanone ml | Cosolvent ml | Cosolvent Type | Hydrogenation Cat. g | Hydrogenation Cat. % by Wt. Ref. to NDHA | Activated Carbon g | Activated Carbon % by Wt. Ref. to NDHA | CPPD | ADA | Ketimine | NDHA |
|---|---|---|---|---|---|---|---|---|---|---|---|---|
| 46 | 10 | 50 | 50 | Methanol | 0.6 | 0.3 | — | — | 25.2 | 25.6 | 48.5 | ~3 |
| 47 | 20 | 100 | 100 | Methanol | 0.6 | 0.15 | 10 | 50 | 94.5 | 0.8 | 1.5 | <0.1 |
| 48 | 30 | 150 | 150 | Methanol | 1.8 | 0.30 | 10 | 33 | 96.5 | <0.1 | <0.2 | <0.1 |
| 49 | 40 | 200 | 200 | Methanol | 1.8 | 0.225 | 10 | 25 | 87.1 | 1.6 | 2.6 | ~1 |
| 50 | 50 | 250 | 250 | Methanol | 1.8 | 0.18 | 20 | 40 | 95.8 | 0.2 | 0.5 | <0.1 |
| 51 | 60 | 300 | 250 | Methanol | 2.16 | 0.18 | 20 | 33 | 90.1 | 2.9 | 4.8 | ~0.5 |
| 52 | 70 | 350 | 250 / 100 | Methanol / Ethanol | 2.16 | 0.15 | 35 | 50 | 93.5 | 0.6 | 0.95 | <0.1 |
| 53 | 80 | 400 | 250 / 150 | Methanol / Ethanol | 2.16 | 0.135 | 35 | 43.7 | 83.5 | 3.9 | 5.8 | ~1 |
| 54 | 90 | 450 | 250 / 200 | Methanol / Ethanol | 2.16 | 0.12 | 50 | 55 | 91.5 | 0.9 | 1.2 | ~0.5 |
| 55 | 100 | 500 | 250 / 250 | Methanol / Ethanol | 2.16 | 0.108 | 100 | 100 | 93.5 | ~0.5 | 0.7 | <0.1 |

CPPD = N-phenyl-N'-cyclohexyl-para-phenylene diamine

COMPARATIVE EXAMPLE 56

This example is a reproduction of Example 1 of British Patent No. 1,295, 672.

50 g of para-nitroso-diphenylhydroxylamine (NDHA), together with 5 g of catalyst consisting of 3% of palladium on activated carbon (E10R, Degussa), corresponding to 0.3% palladium, based on the NDHA in 790 ml of acetone are suspended in a 2 liter autoclave of refined steel, equipped with a horsehoe mixer, a gas supply tube, a manometer, a high-pressure relief valve, and a bottom discharge valve. After the autoclave has been carefully freed of traces of oxygen, a hydrogen pressure of 50 bar was applied and the reaction commenced by heating to 60° C. (heat-up time 15 min.). After the temperature is maintained at 60° C. for 1 hour, it is raised to 150° C. within 30 minutes, then reduced to 95° C. (15 min.) and left at 95° C. for 6 hours. Subsequently, the reactor is cooled down and the catalyst separated from the content by filtration under hydrogen as protective gas. After the solvent is distilled off, obtained by gas chromatography, are compiled in Table VI.

Table VI

| Example No. | MIBK ml. | Cosolvent | | Platinum Cat. | | Act. Carbon | | Conversion NDHA | ADA % by Wt. | Ketimine % by Wt. | DBPPD % by Wt. |
|---|---|---|---|---|---|---|---|---|---|---|---|
| | | g | % Ref. to NDHA | g | % Pt Ref. to NDHA | g | Ref. to NDHA | | | | |
| 57 | 200 | water 20 | 100 | 0.20 | 0.05 | 20 | 100 | 100 | 2.4 | 1.0 | 91.5 |
| 58 | 200 | water 20 | 100 | 0.40 | 0.10 | 10 | 50 | 100 | 0.6 | 1.2 | 92.5 |
| 59 | 200 | water 20 | 200 | 0.80 | 0.20 | 5 | 25 | 100 | 0.05 | 0.6 | 93.5 |
| 60* | 200 | water 20 | 100 | 0.20 | 0.05 | — | — | 95 | 56.8 | 4.0 | 33.1 |
| 61* | 200 | water 20 | 100 | 0.40 | 0.10 | — | — | 100 | 48.9 | 1.8 | 44.0 |
| 62* | 200 | water 20 | 100 | 0.80 | 0.20 | — | — | 100 | 33.7 | 1.5 | 59.4 |
| 63* | 200 | — | — | 0.20 | 0.05 | — | — | 100 | 56.5 | 9.8 | 28.8 |
| 64* | 120 | methanol 80 | 400 | 0.20 | 0.05 | — | — | 100 | 41.3 | 7.7 | 44.2 |
| 65* | 150 | 3-methylpentanol-2 50 | 250 | 0.20 | 0.05 | — | — | 90 | 63.1 | 8.2 | 21.2 |
| 66 | 200 | — | — | 0.20 | 0.05 | 20 | 100 | 100 | 0.65 | 0.9 | 92.9 |
| 67 | 120 | methanol 80 | 400 | 0.20 | 0.05 | 20 | 100 | 100 | 1.9 | 2.3 | 89.1 |
| 68 | 150 | 3-methylpentanol-2 50 | 250 | 0.20 | 0.05 | 20 | 100 | 100 | 2.2 | 2.8 | 88.6 |

*Comparative Examples
ADA = 4-aminodiphenyl,
DBPPD = N-(1,3-dimethylbutyl)-N'-phenyl-para-phenylene diamine 93.25% (based on the desired N-isopropyl-N'-phenyl-para-phenylene diamine (IPPD)) of a grayish brown solid substance remains. The reaction mixture is subjected to a quantitative analysis and determined to contain the following components:

| | |
|---|---|
| N-isopropyl-N'-phenyl-para-phenylene diamine | 77.90% |
| N-isopropyl-N'-cyclohexyl-para-phenylene diamine | 6.95% |
| 4-amino-diphenylamine | 2.10% |
| N,N'-diisopropyl-para-phenylene diamine | 0.96% |
| N-phenyl-N,N'-diisopropyl-para-phenylene diamine | 0.95% |
| N-phenyl-N'-diisopropyl-para-phenylene diamine | 0.65% |
| para-anilinocyclohexanone | 0.65% |

In addition, the mixture is found to contain 2.84% of polymeric compounds, which are comprised predominately of 4-isopropylamino-diphenylamine units. Special mention must be made of the compounds which are hydrogenated in the nucleus, formed under the high pressure and temperature, the separation of which from the desire N-isopropyl-N'-phenyl-para-phenylene diamine is very difficult. Furthermore, about 18% of the charged acetone is converted to isopropanol.

EXAMPLES 57 THROUGH 68

In the manner described for Examples 1 through 9, 20 g (93.2 mmol) of para-nitroso-diphenylhydroxylamine (NDHA) are reacted with methylisobutyl ketone (MIBK) in the presence of a sulfidized platinum catalyst (F103RS of the firm Degussa, platinum sulfide endowment of 5%, by weight) at a temperature of no more than 100° C. and under a hydrogen pressure of 9 to 10 bar. The stirring velocity is 1500 rpm and the reaction time is 45 minutes. The activated carbon has a specific surface area of 1050 m²/g and an ash content of 0.6% ("purest" activated carbon of the firm Merck).

Pressure is removed from the autoclave after cooling to 40° to 50° C. and the catalyst, and, if necessary, the activated carbon are filtered off under a slight nitrogen pressure. The other process parameters and the quantitative composition of the resulting reaction mixtures, as obtained by gas chromatography, are compiled in Table VI.

What we claim is:

1. In an improved process for the preparation of asymmetrical N-phenyl-N'-substituted para-phenylene diamines by the reductive alkylation of para-nitroso-diphenylhydroxylamine with an aldehyde or a ketone in the presence of hydrogen and a hydrogenation catalyst, the improvement comprising utilizing as the hydrogenation catalyst (1) one member selected from the group consisting of palladium and platinum sulfide, in an amount less than 1%, by weight based on the weight of para-nitroso-diphenylhydroxylamine, and (2) activated carbon with a specific surface area of at least 700 square meters per gram and an ash content of less than 7.5%, by weight, in an amount from about 10 to about 200%, by weight based on the weight of para-nitroso-diphenylhydroxylamine.

2. The process of claim 1 wherein the palladium or platinum sulfide is present in an amount from about 0.05 to about 0.2%, by weight based on the weight of para-nitroso-diphenylhydroxylamine.

3. The process of claim 1 or 2 wherein the aldehyde or ketone is utilized in an amount from about 2 to about 10 equivalents, per equivalent of para-nitroso-diphenylhydroxylamine.

4. The process of claim 1 wherein the reductive alkylation is performed in the presence of an inert solvent.

5. The process of claim 3 wherein the reductive alkylation is performed in the presence of an inert solvent.

6. The process of claim 4 wherein the inert solvent is selected from the group consisting of methanol, ethanol, isopropanol, propanol, butanol, and pentanols.

7. The process of claim 5 wherein the inert solvent is selected from the group consisting of methanol, ethanol, isopropanol, propanol, butanol, and pentanols.

8. The process of claim 1 wherein the reductive alkylation is performed at a temperature from about 25° to about 125° C., and at a hydrogen pressure from about 1 to about 150 bar.

9. The process of claim 7 wherein the reductive alkylation is performed at a temperature from about 25° to about 125° C., and at a hydrogen pressure from about 1 to about 150 bar.

10. The process of claim 1 wherein the reductive alkylation is performed at a temperature from about 40° to about 100° C. and at a hydrogen pressure from about 7 to about 12 bar.

11. The process of claim 7 wherein the reductive alkylation is performed at a temperature from about 40° to about 100° C. and at a hydrogen pressure from about 7 to about 12 bar.

* * * * *